(12) United States Patent
Gibson

(10) Patent No.: US 9,623,221 B2
(45) Date of Patent: Apr. 18, 2017

(54) APPARATUS FOR DELIVERY OF PHARMACEUTICALS TO THE COCHLEA

(71) Applicant: Cochlear Limited, Macquarie University (AU)

(72) Inventor: Peter Gibson, South Coogee (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 15/007,876

(22) Filed: Jan. 27, 2016

(65) Prior Publication Data
US 2016/0136400 A1    May 19, 2016

Related U.S. Application Data

(63) Continuation of application No. 14/093,287, filed on Nov. 29, 2013, now abandoned, which is a
(Continued)

(30) Foreign Application Priority Data

Nov. 14, 2000 (AU) .......................................... 1484

(51) Int. Cl.
   *A61N 1/05*        (2006.01)
   *A61M 31/00*     (2006.01)
   (Continued)

(52) U.S. Cl.
CPC .......... *A61M 31/00* (2013.01); *A61M 31/002* (2013.01); *A61N 1/0541* (2013.01); *A61N 1/08* (2013.01); *A61N 1/32* (2013.01); *A61N 1/36032* (2013.01); *A61M 25/00* (2013.01); *A61M 2205/054* (2013.01); *A61M 2210/0662* (2013.01); *A61M 2210/0668* (2013.01);
(Continued)

(58) Field of Classification Search
CPC ................ A61M 31/002; A61M 25/00; A61M 2205/054; A61M 2210/0662; A61M 2210/0668; A61N 1/0541; A61N 1/0568; A61N 1/0574; A61N 1/0575; Y10T 29/49885
USPC ...................................... 607/136–137, 55–56
See application file for complete search history.

(56) References Cited

U.S. PATENT DOCUMENTS 3,887,699 A    6/1975   Yolles
3,890,977 A    6/1975   Wilson
(Continued)

FOREIGN PATENT DOCUMENTS

DE        10032000 A1    1/2001
EP         0002068 A2     5/1979
(Continued)

OTHER PUBLICATIONS

Notice of Reason(s) for Rejection, Japanese Patent Application No. P2002-543261, Jan. 9, 2007.
(Continued)

*Primary Examiner* — Paula J Stice
(74) *Attorney, Agent, or Firm* — Edell, Shapiro & Finnan, LLC

(57) ABSTRACT

An implantable electrode array assembly configured to stimulate tissue of a recipient, including an elongate member configured to be inserted into a recipient, wherein at least a portion of the elongate member includes a bio-active substance.

18 Claims, 3 Drawing Sheets

Related U.S. Application Data continuation of application No. 13/288,763, filed on Nov. 3, 2011, now abandoned, which is a continuation of application No. 12/535,374, filed on Aug. 4, 2009, now Pat. No. 8,401,674, which is a continuation of application No. 10/416,634, filed as application No. PCT/AU01/01479 on Nov. 14, 2001, now Pat. No. 7,571,012.

(51) Int. Cl.
 *A61N 1/08* (2006.01)
 *A61N 1/32* (2006.01)
 *A61N 1/36* (2006.01)
 *A61M 25/00* (2006.01)

(52) U.S. Cl.
 CPC . *A61M 2210/0675* (2013.01); *Y10T 29/49117* (2015.01); *Y10T 29/49885* (2015.01)

(56) References Cited

U.S. PATENT DOCUMENTS

| | | | |
|---|---|---|---|
| 4,046,151 A | 9/1977 | Rose | |
| 4,154,247 A | 5/1979 | O'Neill | |
| 4,306,563 A | 12/1981 | Iwatschenko | |
| 4,351,337 A | 9/1982 | Sidman | |
| 4,357,497 A | 11/1982 | Hochmair et al. | |
| 4,381,013 A | 4/1983 | Dutcher | |
| 4,506,680 A | 3/1985 | Stokes | |
| 4,532,930 A | 8/1985 | Crosby et al. | |
| 4,577,642 A | 3/1986 | Stokes | |
| 4,762,135 A | 8/1988 | van der Puije et al. | |
| 4,784,161 A | 11/1988 | Skalsky et al. | |
| 4,819,662 A | 4/1989 | Heil, Jr. et al. | |
| 4,844,099 A | 7/1989 | Skalsky et al. | |
| 4,972,848 A | 11/1990 | Di Domenico et al. | |
| 4,994,069 A | 2/1991 | Ritchart et al. | |
| 5,066,278 A | 11/1991 | Hirschberg et al. | |
| 5,077,352 A | 12/1991 | Elton | |
| 5,092,332 A | 3/1992 | Lee et al. | |
| 5,120,322 A | 6/1992 | Davis et al. | |
| 5,262,608 A | 11/1993 | Mustonen | |
| 5,265,608 A | 11/1993 | Lee et al. | |
| 5,458,631 A | 10/1995 | Xavier | |
| 5,474,542 A | 12/1995 | Gandi et al. | |
| 5,531,780 A | 7/1996 | Vachon | |
| 5,554,114 A | 9/1996 | Wallace et al. | |
| 5,645,585 A | 7/1997 | Kuzma | |
| 5,653,742 A * | 8/1997 | Parker | A61D 7/00 607/116 |
| 5,697,951 A | 12/1997 | Harpstead et al. | |
| 5,736,251 A | 4/1998 | Pinchuk | |
| 5,755,474 A | 5/1998 | Slomski | |
| 5,755,765 A | 5/1998 | Hyde et al. | |
| 5,769,077 A | 6/1998 | Lindegren | |
| 5,782,744 A | 7/1998 | Money | |
| 5,800,500 A | 9/1998 | Spelman et al. | |
| 5,902,329 A | 5/1999 | Hoffmann et al. | |
| 5,929,041 A | 7/1999 | Magal | |
| 5,957,966 A | 9/1999 | Schroeppel et al. | |
| 5,975,085 A | 11/1999 | Rise | |
| 6,038,482 A | 3/2000 | Vachon | |
| 6,038,483 A | 3/2000 | KenKnight et al. | |
| 6,038,484 A | 3/2000 | Kuzma | |
| 6,078,841 A | 6/2000 | Kuzma | |
| 6,086,582 A * | 7/2000 | Altman | A61B 18/1492 606/41 |
| 6,119,044 A | 9/2000 | Kuzma | |
| 6,125,302 A | 9/2000 | Kuzma | |
| 6,163,729 A | 12/2000 | Kuzma | |
| 6,259,951 B1 | 7/2001 | Kuzma et al. | |
| 6,304,787 B1 | 10/2001 | Kuzma et al. | |
| 6,309,410 B1 * | 10/2001 | Kuzma | A61N 1/0541 607/137 |
| 6,321,125 B1 | 11/2001 | Kuzma | |
| 6,398,758 B1 | 6/2002 | Jacobsen et al. | |
| 6,421,569 B1 | 7/2002 | Treaba et al. | |
| 6,936,040 B2 | 8/2005 | Kramm et al. | |
| 7,044,942 B2 | 5/2006 | Jolly et al. | |
| 7,206,639 B2 | 4/2007 | Jacobsen et al. | |
| 7,272,449 B2 | 9/2007 | Dadd et al. | |
| 7,571,012 B2 | 8/2009 | Gibson | |
| 2001/0053872 A1* | 12/2001 | Zilberman | A61N 1/36032 600/25 |
| 2002/0032468 A1* | 3/2002 | Hill | A61N 1/0517 607/2 |
| 2002/0032477 A1 | 3/2002 | Helmus et al. | |
| 2002/0077685 A1 | 6/2002 | Sundquist et al. | |
| 2003/0045921 A1 | 3/2003 | Dadd et al. | |
| 2003/0097121 A1 | 5/2003 | Jolly et al. | |
| 2003/0181967 A1 | 9/2003 | Dadd et al. | |
| 2004/0030376 A1 | 2/2004 | Gibson et al. | |
| 2004/0078057 A1 | 4/2004 | Gibson | |
| 2004/0116995 A1 | 6/2004 | Dadd | |
| 2004/0122501 A1 | 6/2004 | Dadd et al. | |
| 2005/0177118 A1 | 8/2005 | Hoganson et al. | |
| 2005/0256560 A1 | 11/2005 | Lenarz et al. | |
| 2006/0287689 A1 | 12/2006 | Debruyne et al. | |
| 2007/0184085 A1 | 8/2007 | Radhakrishnan et al. | |
| 2008/0033520 A1 | 2/2008 | Jolly | |
| 2009/0048580 A1 | 2/2009 | Gibson | |
| 2009/0062896 A1 | 3/2009 | Overstreet et al. | |
| 2009/0076581 A1 | 3/2009 | Gibson | |
| 2009/0292237 A1 | 11/2009 | Overstreet et al. | |

FOREIGN PATENT DOCUMENTS

| | | |
|---|---|---|
| EP | 0 007 157 A2 | 1/1980 |
| EP | 0350188 A1 | 1/1990 |
| EP | 0602859 A2 | 6/1994 |
| EP | 0653223 A2 | 5/1995 |
| EP | 0 706 807 A2 | 4/1996 |
| EP | 0739642 A2 | 10/1996 |
| EP | 0773037 A2 | 5/1997 |
| EP | 0778043 A1 | 6/1997 |
| EP | 0778044 A2 | 6/1997 |
| EP | 0783900 A2 | 7/1997 |
| EP | 0784994 A1 | 7/1997 |
| EP | 0784995 A1 | 7/1997 |
| EP | 0919254 A2 | 6/1999 |
| EP | 0783901 B1 | 4/2003 |
| GB | 2217993 A | 11/1989 |
| JP | 55-190 | 5/1980 |
| JP | 8-229137 | 9/1996 |
| JP | 9-508054 | 8/1997 |
| JP | 11-514252 | 11/1999 |
| WO | 96/15665 | 5/1996 |
| WO | 97/10784 | 3/1997 |
| WO | 9900067 A1 | 1/1999 |
| WO | 9911321 | 3/1999 |
| WO | 9955360 A1 | 11/1999 |
| WO | 00/56399 | 9/2000 |
| WO | 0057949 A1 | 10/2000 |
| WO | 0071063 A1 | 11/2000 |
| WO | 0141674 A1 | 6/2001 |
| WO | 0197908 A2 | 12/2001 |
| WO | 0224064 A1 | 3/2002 |
| WO | 0232498 A1 | 4/2002 |
| WO | 0241666 A1 | 5/2002 |
| WO | 02055136 A2 | 7/2002 |
| WO | 02083234 A1 | 10/2002 |
| WO | 02087681 A2 | 11/2002 |
| WO | 03049658 A1 | 6/2003 |
| WO | 03072193 A1 | 9/2003 |
| WO | 2009124041 A1 | 10/2009 |
| WO | 2010045432 A2 | 4/2010 |

OTHER PUBLICATIONS

Australian Examination Report. Patent Application No. 2007202203. Mailed Oct. 22, 2008.

(56) References Cited

OTHER PUBLICATIONS

International Search Report dated Nov. 19, 2001; corresponding PCT/AU01/01479 filed Dec. 2, 2001 published as WO 02/41666 on May 23, 2002; Applicant: Cochlear Limited; Inventors: Peter Gibson.
Written Opinion dated Jan. 28, 2002; corresponding PCT/AU01/01479 filed Dec. 2, 2001 published as WO 02/41666 on May 23, 2002; Applicant: Cochlear Limited; Inventors: Peter Gibson.
International Preliminary Examination Report dated Oct. 4, 2002; corresponding PCT/AU01/01479 filed Dec. 2, 2001 published as WO 02/41666 on May 23, 2002; Applicant: Cochlear Limited; Inventors: Peter Gibson.
Supplemental European Search Report. EP 01994538. Mailed May 27, 2005.
Altschulere, et al., "Rescue and Regrowth of Sensory Nerves Following Deafferentation by Neurotrophic Factors," Annals New York Academy of Sciences.
http://www.merriam-webster.com/dictionary/lumen accessed Mar. 28, 2011.
hittp://www.merriam-webster.com/dictionary/lumen accessed Mar. 28, 2011.
K. Mason Publications Ltd., "Epicardiai-Transvenous Left Ventricular Lead with Dual Ring Electrodes (Cathode Ring & Anode Ring) Design", Research Disclosure, Disclosed Anonymously, Nov. 1997, No. 403-40349, pp. 790-791.
"Epicardiai-Transvenous Left Ventricular Lead with Wound Butterfly Electrode", Research Disclosure, Nov. 1997, No. 403-40342, pp. 785.
European Application No. 08253298.7, Office Action mailed on Jul. 14, 2010.
European Application No. 08253298.7, Office Action mailed on Nov. 6, 2009.
European Application No. 08253298.7, Response to Office Action mailed on Mar. 16, 2010.
U.S. Appl. No. 10/416,634, Notice of Allowance mailed on Dec. 11, 2008, 9 Pages.
U.S. Appl. No. 10/416,634, Notice of Allowance mailed on Mar. 27, 2009, 6 Pages.
U.S. Appl. No. 10/416,634, Office Action mailed on Apr. 6, 2006, 24 Pages.
U.S. Appl. No. 10/416,634, Office Action mailed on Oct. 4, 2006, 20 Pages.
U.S. Appl. No. 10/416,634, Office Action mailed on Oct. 1, 2007, 29 Pages.
U.S. Appl. No. 10/416,634, Office Action mailed on Feb. 28, 2007, 27 Pages.
U.S. Appl. No. 10/416,634, Office Action mailed on May 19, 2008, 10 Pages.
U.S. Appl. No. 10/536,714, Office Action mailed on Apr. 6, 2009, 13 Pages.
U.S. Appl. No. 10/536,714, Office Action mailed on Nov. 17, 2009, 12 Pages.
U.S. Appl. No. 10/536,714, Office Action mailed on May 6, 2010, 9 Pages.
U.S. Appl. No. 10/536,714, Office Action mailed on Dec. 30, 2010, 14 Pages.
U.S. Appl. No. 12/191,302, Office Action mailed on Jun. 3, 2009, 10 Pages.
U.S. Appl. No. 12/191,302, Office Action mailed on Dec. 24, 2009, 18 Pages.
U.S. Appl. No. 12/191,302, Office Action mailed on Sep. 15, 2010, 12 Pages.
U.S. Appl. No. 12/191,302, Office Action mailed on Mar. 14, 2011, 18 Pages.
Australian Application No. 2002223270, First Examination Report mailed on Aug. 17, 2005.
Australian Application No. 2003205441, First Examination Report mailed on Dec. 6, 2006.
Australian Application No. 2003283124, First Examination Report mailed on Jun. 13, 2008.
Canadian Application No. 2,428,542, Office Action mailed on May 15, 2009.
Canadian Application No. 2,477,148, Requisition mailed on Aug. 31, 2009.
European Application No. 01973835.0, Supplemental Search Report mailed on Jan. 22, 2004, 3 Pages.
European Application No. 01994538.5, Examination Report mailed on Apr. 20, 2007, 4 Pages.
European Application No. 03702212.6, Examination Report mailed on Aug. 7, 2008, 5 Pages.
European Application No. 03702212.6, Supplementary Search Report mailed on Jun. 23, 2006, 4 Pages.
European Application No. 08253298.7, Extended Report mailed on Jan. 14, 2009, 5 Pages.
Japanese Application No. 2003-570935, Notification of Reasons for Refusal (Translation) mailed on Jul. 22, 2008.
International Application No. PCT/AU2001/01230, International Preliminary Examination Report mailed on Nov. 27, 2001, 3 Pages.
International Application No. PCT/AU2001/01230, International Search Report mailed on Oct. 26, 2001, 3 Pages.
International Application No. PCT/AU2001/01231, International Search Report mailed on Oct. 26, 2001, 3 Pages.
International Application No. PCT/AU2001/01232, International Preliminary Examination Report mailed on Feb. 25, 2002, 3 Pages.
International Application No. PCT/AU2001/01232, International Search Report mailed on Oct. 26, 2001, 2 Pages.
International Application No. PCT/AU2003/000248, International Preliminary Examination Report mailed on Jun. 2, 2004, 4 Pages.
International Application No. PCT/AU2003/000248, International Search Report mailed on Apr. 7, 2003, 3 Pages.
International Application No. PCT/AU2003/001584, At 2nd Office Action and English Translation mailed on Mar. 20, 2007.
International Application No. PCT/AU2003/001584, International Preliminary Examination Report mailed on Mar. 15, 2005, 6 Pages.
International Application No. PCT/AU2003/001584, International Search Report mailed on Apr. 2, 2004, 3 Pages.
International Application No. PCT/US2009/038942, International Search Report mailed on May 28, 2009, 2 Pages.
International Application No. PCT/US2009/038942, Written Opinion mailed on May 28, 2009, 11 Pages.
PR 0541, Australian Search Report mailed on Dec. 20, 2000.
PR 0542, Australian Search Report mailed on Dec. 20, 2000.
PR 0684, Australian Search Report mailed on Dec. 20, 2000.
PR 0807, Australian Search Report mailed on Dec. 20, 2000.
PR 1005, Australian Search Report mailed on Dec. 20, 2000.

\* cited by examiner

APPARATUS FOR DELIVERY OF PHARMACEUTICALS TO THE COCHLEA

CROSS-REFERENCE TO RELATED APPLICATIONS

The present application is a continuation of U.S. patent application Ser. No. 14/093,287, filed Nov. 29, 2013, which is a continuation of U.S. patent application Ser. No. 13/288,763, filed Nov. 3, 2011, now Abandoned, which is a continuation of U.S. patent application Ser. No. 12/535,374, filed on Aug. 4, 2009, now U.S. Pat. No. 8,401,674, issued on Mar. 19, 2013, which is a continuation of U.S. patent application Ser. No. 10/416,634; filed on Nov. 10, 2003, now U.S. Pat. No. 7,571,012, issued on Aug. 4, 2009, which is a National Stage Application of International Application No. PCT/AU01/01479, filed on Nov. 14, 2001, which claims priority to Australian Provisional Application No. PR 1484, filed on Nov. 14, 2000, the contents of each of these applications being incorporated herein by reference in their entirety.

BACKGROUND

Field of the Invention

The present invention relates to an implantable device and, in particular, to an implantable cochlear electrode assembly.

Related Art

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aid systems, which amplify sound so that acoustic information does reach the cochlea and the hair cells.

In many people who are profoundly deaf, however, the reason for deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibers, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Cochlear implant systems have typically consisted of two key components, namely an external component commonly referred to as a processor unit, and an implanted internal component commonly referred to as a stimulator/receiver unit. Traditionally, both of these components have cooperated together to provide the sound sensation to an implantee.

The external component has traditionally consisted of a microphone for detecting sounds, such as speech and environmental sounds, a speech processor that converts the detected sounds and particularly speech into a coded signal, a power source such as a battery, and an external antenna transmitter coil.

The coded signal output by the speech processor is transmitted transcutaneously to the implanted stimulator/receiver unit situated within a recess of the temporal bone of the implantee. This transcutaneous transmission occurs through use of an inductive coupling provided between the external antenna transmitter coil which is positioned to communicate with an implanted antenna receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of a radio frequency (RF) link, but other such links have been proposed and implemented with varying degrees of success.

The implanted stimulator/receiver unit typically includes the antenna receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

The external componentry of the cochlear implant has been traditionally carried on the body of the implantee, such as in a pocket of the implantee's clothing, a belt pouch or in a harness, while the microphone has been mounted on a clip mounted behind the ear or on a clothing lapel of the implantee.

More recently, due in the main to improvements in technology, the physical dimensions of the speech processor have been able to be reduced allowing for the external componentry to be housed in a small unit capable of being worn behind the ear of the implantee. This unit has allowed the microphone, power unit and the speech processor to be housed in a single unit capable of being discretely worn behind the ear, with the external transmitter coil still positioned on the side of the user's head to allow for the transmission of the coded sound signal from the speech processor and power to the implanted stimulator unit. It is also considered that with continued improvements in technology, it may become possible to provide a system whereby all components of the system are implanted inside the head of the implantee resulting in a system that is completely invisible and does not require any external components to operate, at least for a portion of the time.

Together with improvements in available technology much research has been undertaken in the area of understanding the way sound is naturally processed by the human auditory system. With such an increased understanding of how the cochlea naturally processes sounds of varying frequency and magnitude, there is a need to provide an improved cochlear implant system that delivers electrical stimulation to the auditory nerve in a way that takes into account the natural characteristics of the cochlea.

It is known in the art that the cochlea is tonotopically mapped. In other words, the cochlea can be partitioned into regions, with each region being responsive to signals in a particular frequency range. This property of the cochlea is exploited by providing the electrode assembly with an array of electrodes, each electrode being arranged and constructed to deliver a cochlea stimulating signal within a preselected frequency range to the appropriate cochlea region. The electrical currents and electric fields from each electrode stimulate the cilia disposed on the modiola of the cochlea. Several electrodes may be active simultaneously.

It has been found that in order for these electrodes to be effective, the magnitude of the currents flowing from these electrodes and the intensity of the corresponding electric fields, are a function of the distance between the electrodes and the modiola. If this distance is relatively great, the threshold current magnitude must be larger than if the distance is relatively small. Moreover, the current from each electrode may flow in all directions, and the electrical fields corresponding to adjacent electrodes may overlap, thereby causing cross-electrode interference. In order to reduce the threshold stimulation amplitude and to eliminate cross-electrode interference, it is advisable to keep the distance between the electrode array and the modiola as small as possible. This is best accomplished by providing the electrode array in the shape which generally follows the shape of the modiola. Also, this way the delivery of the electrical stimulation to the auditory nerve is most effective as the electrode contacts are as close to the auditory nerves that are particularly responsive to selected pitches of sound waves.

In order to achieve this electrode array position close to the inside wall of the cochlea, the electrode needs to be designed in such a way that it assumes this position upon or immediately following insertion into the cochlea. This is a challenge as the array needs to be shaped such that it assumes a curved shape to conform with the shape of the modiola and must also be shaped such that the insertion process causes minimal trauma to the sensitive structures of the cochlea. In this sense it has been found to be desirable for the electrode array be generally straight during the insertion procedure.

Several procedures have been adopted to provide an electrode assembly that is relatively straightforward to insert while adopting a curved configuration following insertion in the cochlea. In one case, a platinum wire stylet is used to hold a pre-curved electrode array in a generally straight configuration up until insertion. Following insertion, the platinum stylet is withdrawn allowing the array to return to its pre-curved configuration.

In developing electrode array designs, it is of great importance that the design be constructed to minimize potential damage to sensitive structures in the cochlea upon insertion and placement of the array. While electrode arrays are preferably designed to minimize such damage, the cochlea does suffer a degree of trauma due to the insertion process.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It is a preferred feature of the present invention to provide an electrode assembly that is adapted to assist the cochlea in its recovery from trauma following the insertion of an electrode assembly therein. The present invention is equally applicable to conventional electrode assemblies and electrode assemblies which are designed to conform with the inner wall of the cochlea.

According to a first aspect, the present invention is an implantable tissue-stimulating device comprising: a resiliently flexible elongate member having a plurality of electrodes mounted thereon; and a bio-active substance delivery means adapted to deliver at least one bio-active substance to the implantee following implantation of the device.

In a preferred embodiment of this invention, the device is a cochlear implant electrode assembly.

In one embodiment, the substance delivery means can comprise at least a portion of the elongate member that has been impregnated with a bio-active substance that can leach therefrom following implantation.

In a further embodiment, the elongate member preferably has a first end that is firstly inserted into the implantee.

In another embodiment, the substance delivery means can include a lumen extending through the elongate member for at least a portion of its length. The lumen can be cylindrical or have any other suitable cross-sectional shape. In one embodiment, the lumen extends through the elongate member for a substantial portion of its length. In a further embodiment, the lumen extends from an opening distal the first end to a position that is at or adjacent the first end. The distal opening of the lumen preferably can be closed by a closure means adapted to seal the opening of the lumen.

The closure means can comprise a plug adapted to be inserted into the lumen and to form a seal therewith. The plug can have a frusto-conical outer wall adapted to seal with the wall of the lumen on insertion. The plug in this embodiment can be formed from a resiliently flexible material such as silicone or polyurethane. Alternatively, the plug could be of any suitable shape and could also be formed from a stiff plastic, such as polytetrafluoroethylene (PTFE), or a metal, such as platinum or stainless steel.

In another embodiment, the closure means can comprise a cap adapted to seal the distal opening of the lumen. In one embodiment, the cap can have a top adapted to seal the opening and a skirt depending therefrom. The skirt can have an engagement means formed on an outer surface thereof adapted to engage with the inner surface of the lumen on mounting of the cap to the lumen. In this embodiment, the inner surface of the lumen can have an engagement means complementary to that on the outer surface of the skirt of the cap. The engagement means on the skirt can comprise a screw thread adapted to engage with a corresponding screw thread on the inner cylindrical surface of the lumen.

The lumen in the elongate member can act as a reservoir for a bio-active substance within the elongate member. In one embodiment, the bio-active substance in the reservoir can leach from the lumen into the outer surface of the member that is preferably close to the desired site of action for the bio-active substance. In another embodiment, the elongate member can have one or more substance egress means whereby the substance can move out of the lumen and the elongate member to a position that is preferably close to the desired site of action for the bio-active substance.

Where the bio-active substance is carried in or comprises a fluid, each substance egress means preferably comprises a fluid egress means.

Each fluid egress means preferably has a valve means that allows fluid to exit the lumen but prevents, or at least substantially prevents, fluid flow from external the elongate member back into the lumen within the elongate member.

In a further embodiment, the distal opening of the lumen can be in fluid communication with an additional reservoir for the bio-active substance that is external to the elongate member. A pumping means, such as an osmotic pump, can transfer the bio-active substance from the additional reservoir into the lumen of the elongate member for subsequent delivery to the appropriate site of action.

It is also envisaged that the bio-active substance can be captured in the form of a solid pellet 55. In one embodiment shown in FIG. 5, the solid pellet 55 can be formed by impregnating the bio-active substance in a ceramic or a polymer pellet that has a predetermined rate of release of the bioactive substance. This solid pellet 55 can then be stored in the lumen reservoir or in an external reservoir connectable to the lumen.

In one embodiment, the bioactive substance can comprise a steroid. In another embodiment, the bioactive substance can perform a function of reducing the resting neuron potential of neurons within the cochlea. The use of such substances can result in less energy being required to excite the neurons and cause stimulation.

In a further embodiment, the elongate member can have a first configuration selected to allow said member to be inserted into an implantee's body, such as the cochlea, and a second configuration wherein said elongate member is adapted to apply a preselected tissue stimulation with the electrodes. In a further embodiment, the elongate member can have at least one intermediate configuration between said first and second configurations.

In a still further embodiment shown in FIG. 5, at least a portion of the outer surface can have a coating of lubricious material 57. In a further embodiment, a substantial portion of the outer surface can have a coating of the lubricious material 57. In a still further embodiment, the entire outer surface of the elongate member can have a coating of the lubricious material 57.

The lubricious material 57 preferably becomes lubricious on being brought into contact with a fluid, such as a saline solution. Still further, the coating 57 preferably becomes lubricious on being brought into contact with a body fluid, such as cochlear fluid.

In one embodiment, the lubricious material 57 is selected from the group comprising polyacrylic acid (PAA), polyvinyl alcohol (PVA), polylactic acid (PLA) and polyglycolic acid (PGA). It is envisaged that other similar materials could also be used. It is envisaged that the lubricious material 57 can also be impregnated with the bio-active substance allowing the coating to perform a dual role. The rate of delivery of the bio-active substance can be programmed by design of the coating structure.

In yet another embodiment, the device can include a stiffening element made of a second material relatively stiffer than the resiliently flexible material of the elongate member. The stiffening element can be adapted to bias the elongate member into the first configuration.

In a still further embodiment, the device can include a stiffening sheath that envelops said elongate member and which is made of a material that is relatively stiffer than the resiliently flexible material of the elongate member. The stiffening sheath can be adapted to bias the elongate member into the first configuration. In one embodiment, the stiffening sheath can be overlaid by the coating of lubricious material.

Where both the stiffening element and stiffening sheath are present in the device, the element and sheath can be adapted in combination to bias said elongate member into said first configuration. In this embodiment, if either the stiffening element or the stiffening sheath is removed or deactivated, the elongate member can adopt said at least one intermediate configuration. In this embodiment, the stiffening sheath can be formed of the same material or a different material to that of the stiffening element. In either case, the stiffening sheath can be relatively more stiffer or relatively less stiffer than the stiffening element.

In a preferred embodiment, the second configuration of the elongate configuration when in the second configuration.

The elongate member is preferably preformed from a plastics material with memory and is preformed to the second configuration.

In a preferred embodiment, the first configuration is preferably substantially straight. More preferably, the first configuration is straight.

In a preferred embodiment, the elongate member is formed from a suitable biocompatible material. In one embodiment, the material can be a silicone, such as Silastic MDX 4-4210. In another embodiment, the elongate member can be formed from a polyurethane or similar material.

In one embodiment, the stiffening element is formed of a bioresorbable material which softens or dissolves on exposure to a fluid. The stiffening element can soften or dissolve on exposure to a saline solution or a body fluid of the implantee, such as cochlear fluid.

In a further embodiment, the bioresorbable material of the stiffening element is selected from the group comprising polyacrylic acid (PAA), polyvinyl alcohol (PVA), polylactic acid (PLA) and polyglycolic acid (PGA). It is envisaged that other similar materials could also be used. It is envisaged that the bioresorbable material of the stiffening element can also be impregnated with one or more of the bio-active substances allowing the stiffening element to perform a dual role. The rate of delivery of the bioactive substance can be determined by the structural design of, or the materials used in, the stiffening element structure.

In another embodiment, the stiffening element can be formed from a non-bioresorbable material. In this embodiment, the stiffening element can comprise a metallic stylet, or a stylet-like element formed from any other suitable stiffening material, extending through a lumen in the elongate member. In one embodiment, the wire can be formed from a biocompatible metal, a biocompatible metallic alloy or a biocompatible relatively stiff plastic. In a preferred embodiment, a metal stylet can be formed from platinum.

In a still further embodiment, the stiffening element can be formed from a shape memory or heat sensitive material. For example, the stiffening element can be formed from a bimetallic element (such as nickel/titanium) and shaped to take a straight or substantially straight configuration at room temperature but bend into another shape on exposure to body temperature (eg. about 37 .degree. C.).

The lumen for the stylet can be the same lumen as utilized in one embodiment of the substance delivery means defined above. In another embodiment, the lumen can be a different lumen to that utilized as part of the substance delivery means defined above. The lumen for the stylet can be cylindrical and also can have an opening formed therein. In the case of a metal stylet, the stylet can extend out of the opening allowing the stylet to be manipulated and removed from the lumen during or following insertion of the device. In the case of a bioresorbable stiffening element, the opening can act as a fluid ingress means allowing body fluids to enter the lumen on insertion of the device into an implantee.

The stiffening sheath, if present, can be formed of a bioresorbable material which dissolves or softens on exposure to a fluid. The stiffening sheath can dissolve or soften on exposure to a saline solution or a body fluid of the implantee, such as cochlear fluid and in doing so also release one or more bio-active substances impregnated therein.

In a further embodiment, the bioresorbable material of the stiffening sheath is selected from the group comprising polyacrylic acid (PAA), polyvinyl alcohol (PVA), polylactic acid (PLA) and polyglycolic acid (PGA). It is envisaged that other suitable materials could also be used. It is envisaged that the bioresorbable element of the stiffening sheath can also be impregnated with one or more bio-active substances allowing the stiffening sheath to perform a dual role. The rate of delivery of the bio-active substance can be set by the structural design of, or the materials used in, the sheath structure.

The device can include an additional layer surrounding the stiffening sheath. The additional layer can have a first rate of fluid ingress therethrough and have at least one fluid ingress means formed therein, the rate of fluid ingress through the fluid ingress means being greater than the first rate of fluid ingress through the additional layer. In this embodiment, the coating of lubricious material can be coated on the outside of the additional layer.

The fluid ingress means can comprise one or more openings in the additional layer. The openings can be closable. The openings can comprise slits in the additional layer. The slits can be formed to allow substantially the same or the same rate of ingress of fluid through the additional layer. In another embodiment, at least one slit can allow a different rate of progress of fluid through the additional layer compared to the other slits. In one embodiment, the slits can be sealable with a bioresorbable material. The bioresorbable material preferably softens and/or dissolves on exposure to a fluid, such as cochlear fluid, to allow ingress of the fluid into the elongate member. In this embodiment, the slits can be sealed with the same or a different quantity and/or the same or different thicknesses of bioresorbable material. Variations in thickness and/or quantity of the bioresorbable material provide a means of varying the rate of ultimate dissolution of the stiffening element of the device, if present, and/or the rate of elution of said at least one bioactive substance.

In another embodiment, the slits can be designed so that when the electrode array is in a straight configuration the slits are closed, preventing the ingress of fluid therethrough. The closure of the slits can be formed by the material of the outer wall, such as silicone, being under compression. When the electrode array is inserted into the cochlea and begins to assume a curved configuration, the slits become open allowing the ingress of fluid therethrough, due in the main to the silicone in the outer wall being released from the state of compression. Such a design allows greater control of the rate of fluid ingress and subsequent dissolution of the stiffening element of the device and/or the elution of said at least one bioactive substance.

The stiffening sheath, if present, can be formed from a shape memory or heat sensitive material. For example, the stiffening sheath can be formed from a bimetallic or alloy filament (such as nickel/titanium) and shaped to take and maintain the straight or substantially straight configuration of the elongate member at room temperature but bend it into another shape once it is exposed to body temperature.

In one embodiment, while both the stiffening element and the stiffening sheath are in position within the device, it will retain the first configuration, which as discussed is preferably straight. If the stiffening sheath is removed or softened, whether it is by dissolution or otherwise, the remaining stiffening element can have insufficient strength to retain the elongate member in its first configuration. It is preferred that the elongate member, on removal or softening of the stiffening sheath, will adopt an intermediate configuration in which the elongate member has at least some curvature.

The present invention provides a surgeon with a cochlear implant electrode array that can assist with the delivery of one or more bio-active substances to the implantation site following its implantation. The substances that can be delivered by the present device include substances that are adapted to promote healing, substances that prevent bleeding or at least excessive bleeding, and also substances that prevent the growth of tissue, including scar tissue, in the cochlea following implantation. Pharmaceutical compounds such as anti-inflammatories and antibiotics can also be delivered by the present device.

It is also envisaged that substances that assist in reducing the resting potential of the surrounding neurons can also be delivered by the present invention. It should be appreciated that during neural stimulation the neurons propagate an action potential through the response of transmembrane ion channels to local electrical fields. By delivering a substance that elicits a change in the transmembrane potential, the resting neural membrane potential can be moved towards the activation potential resulting in a lowering of the energy required to be delivered to activate the neuron. This also has the potential to reduce the power required by the stimulation device as well as increase the specificity of the electrical stimulation and restore the stochastic response of the neurons.

In one embodiment, and where the elongate member is impregnated with a bio-active substance, the device can be formed by a method that includes a step of impregnating the elongate member with the bio-active substance prior to implantation. Impregnation may be achieved by soaking the elongate member in a solution that constitutes or includes the bio-active substance for a period of time. The degree of impregnation can be controlled by the period of time of soaking of the elongate member. It is anticipated that the degree of impregnation will impact on the rate of substance delivery by the device following implantation.

In another embodiment, and where the elongate member includes a lumen acting as a reservoir for a bio-active substance, the lumen can be filled with the bio-active substance prior to implantation. In one embodiment, the lumen can be filled during manufacture and/or packaging of the elongate member. In another embodiment, the lumen can be filled, such as by the surgeon, just prior to implantation. The substance egress means preferably does not allow the bio-active substance to pass from the lumen until the device is ready for implantation or after implantation. In one embodiment, the substance egress means could be activated by the surgeon just prior to its insertion into the implantee. In another embodiment, the substance egress means may be coated with a layer of bioresorbable material that softens and/or dissolves on exposure to a fluid, such as cochlear fluid. Following its dissolution, the bio-active substance is free to pass through the substance egress means.

The device can be adapted to only provide delivery of a bio-active substance to the implantation site for a particular period following implantation. This period may comprise any period of time from a few hours or days to a few weeks or even months. In another embodiment, the device can be used as a means of delivery of bio-active substances to the implantee well beyond the time of implantation. For example, the additional reservoir can be periodically filled with a bio-active substance to ensure continued supply of the bio-active substance to the implantation site. The additional reservoir, in this case, may be positioned beneath but adjacent the surface of the skin of the implantee thereby allowing the reservoir to be filled by a syringe and needle assembly that injects the bio-active substance into the additional reservoir.

Once implanted, the electrodes can receive stimulation signals from a stimulator means. The stimulator means is preferably electrically connected to the elongate member by way of an electrical lead. The lead can include the one or more wires extending from each electrode of the array mounted on the elongate member.

In one embodiment, the lead can extend from the elongate member to a stimulator means or at least the housing thereof. In one embodiment, the lead is continuous with no electrical connectors, at least external the housing of the stimulator means, required to connect the wires extending from the electrodes to the stimulator means. One advantage of this arrangement is that there is no requirement for the surgeon implanting the device to make the necessary electrical connection between the wires extending from the electrodes and the stimulator means.

The stimulator means is preferably positioned within a housing that is implantable within the implantee. The housing for the stimulator means is preferably implantable within the bony well in the bone behind the ear posterior to the mastoid.

When implantable, the housing preferably contains, in addition to the stimulator means, a receiver means. The receiver means is preferably adapted to receive signals from a controller means. The controller means is, in use, preferably mounted external to the body of the implantee such that the signals are transmitted transcutaneously through the implantee.

Signals can preferably travel from the controller means to the receiver means and vice versa. The receiver means can include a receiver coil adapted to receive radio frequency (RF) signals from a corresponding transmitter coil worn externally of the body. The radio frequency signals can comprise frequency modulated (FM) signals. While described as a receiver coil, the receiver coil can preferably transmit signals to the transmitter coil which receives the signals.

The transmitter coil is preferably held in position adjacent the implanted location of the receiver coil by way of respective attractive magnets mounted centrally in, or at some other position relative to, the coils.

The external controller can comprise a speech processor adapted to receive signals output by a microphone. During use, the microphone is preferably worn on the pinna of the implantee, however, other suitable locations can be envisaged, such as a lapel of the implantee's clothing. The speech processor encodes the sound detected by the microphone into a sequence of electrical stimuli following given algorithms, such as algorithms already developed for cochlear implant systems. The encoded sequence is transferred to the implanted stimulator/receiver means using the transmitter and receiver coils. The implanted stimulator/receiver means demodulates the FM signals and allocates the electrical pulses to the appropriate attached electrode by an algorithm which is consistent with the chosen speech coding strategy.

The external controller further comprises a power supply. The power supply can comprise one or more rechargeable batteries. The transmitter and receiver coils are used to provide power via transcutaneous induction to the implanted stimulator/receiver means and the electrode array.

While the implant system can rely on external componentry, in another embodiment, the controller means, including the microphone, speech processor and power supply can also be implantable. In this embodiment, the controller means can be contained within a hermetically sealed housing or the housing used for the stimulator means.

BRIEF DESCRIPTION OF THE DRAWINGS

By way of example only, a preferred embodiment of the invention is now described with reference to the accompanying drawings, in which.

DETAILED DESCRIPTION

Figure 1:
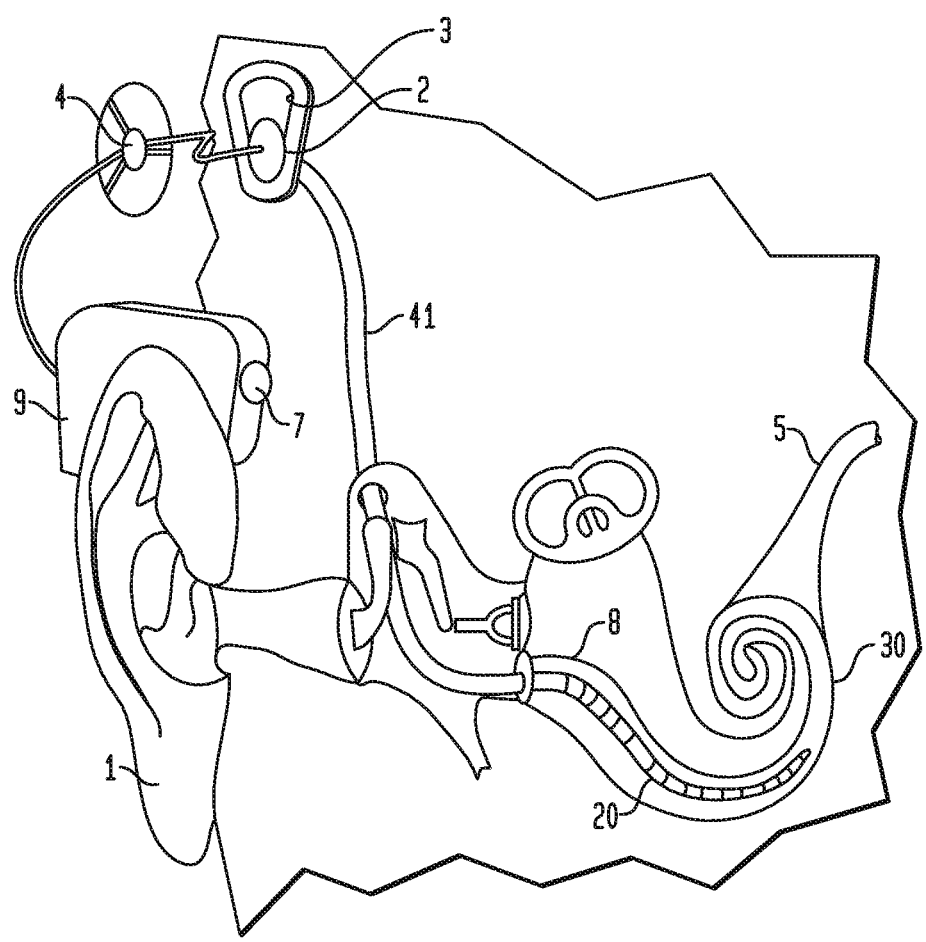
FIG. 1 is a pictorial representation of a prior art cochlear implant system.

Before describing the features of the present invention, it is appropriate to briefly describe the construction of one type of known cochlear implant system with reference to FIG. 1.

Known cochlear implants typically consist of two main components, an external component including a speech processor 9, and an internal component including an implanted receiver and stimulator unit 2. The external component includes a microphone 7. The speech processor 9 is, in this illustration, constructed and arranged so that it can fit behind the outer ear 1. Alternative versions may be worn on the body. Attached to the speech processor 9 is a transmitter coil 4 which transmits electrical signals to the implanted unit 2 via a radio frequency (RF) link.

The implanted component includes a receiver coil 3 for receiving power and data from the transmitter coil 4. A cable 41 extends from the implanted receiver and stimulator unit 2 to the cochlea 30 and terminates in an electrode array 20. The signals thus received are applied by the array 20 to the basilar membrane 8 and the nerve cells within the cochlea 30 thereby stimulating an auditory nerve 5. The operation of such a device is described, for example, in U.S. Pat. No. 4,532,930.

Figure 2:
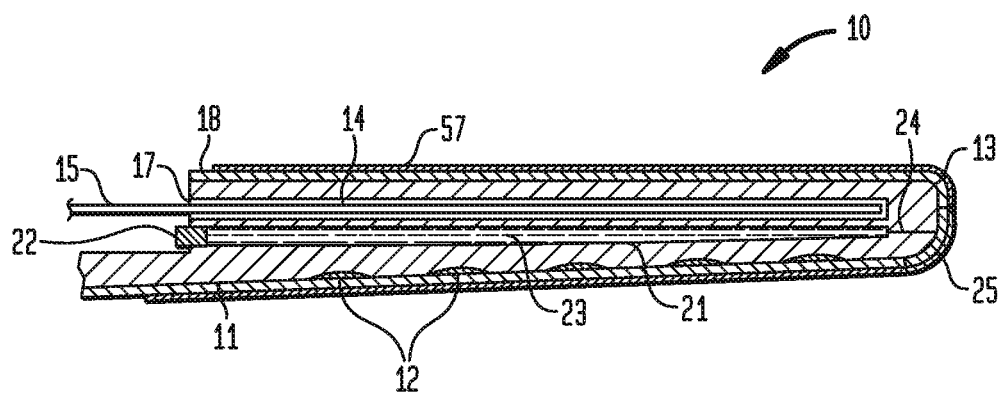
FIG. 2 is a simplified cross-sectional view of one embodiment of an electrode assembly according to the present invention ready for insertion into a cochlea.
Figure 3:
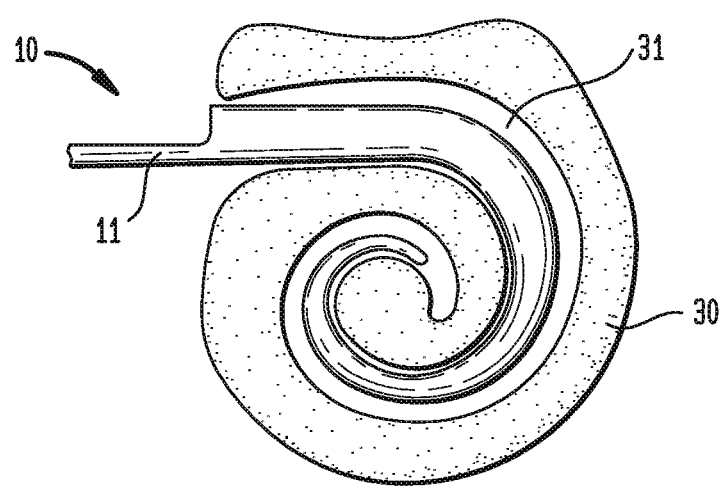
FIG. 3 is a simplified part-sectional, part side elevational view of the electrode assembly depicted following insertion in the cochlea.

One embodiment of a cochlear implant electrode assembly according to the present invention is depicted generally as 10 in FIGS. 2 and 3.

The depicted electrode assembly 10 has an electrical lead extending back to a stimulator/receiver housing, such as the stimulator unit 2 depicted in FIG. 1. In considering this invention, it is to be understood that each electrode 12 may have one or more wires (not depicted) electrically connected thereto and extending from each respective electrode 19 back through the lead to the stimulator/receiver.

The assembly 10 comprises an elongate electrode carrier member 11 having a plurality of electrodes 12 mounted thereon. For the purposes of clarity, the electrodes 12 depicted in FIG. 1 are not necessarily shown to scale. A larger number of electrodes than that depicted in FIG. 2 can also be envisaged. The electrodes 12 are not depicted in FIG. 3 for reasons of clarity.

The depicted elongate member 11 is preformed from a resiliently flexible silicone with memory and is preformed to a curved configuration suitable for insertion in the scala tympani 31 of a human cochlea 30. While an assembly that normally adopts a curved configuration when in a relaxed condition is depicted in the drawings, it will be appreciated that the present invention also could be utilized with respect to assemblies that are normally straight when in a relaxed condition.

The elongate member 11 has a first end 13 that is firstly inserted into the cochlea 30 upon insertion of the assembly 10.

As depicted in FIG. 2, there is disposed within a lumen 14, prior to insertion of the assembly 10 into the cochlea 30, a substantially straight platinum stylet 15. In the depicted embodiment, the stylet 15 has a stiffness that is sufficient to retain the silicone elongate member 11 in a straight configuration. The stylet could be constructed so as to have a stiffness that was insufficient alone to retain the elongate member 11 in a straight configuration. In this case, the elongate member could have a stiffening sheath 18 that at lest partially envelops the elongate member 11. The stiffening sheath 18 could be formed of a bioresorbable material which prior to implantation assists the platinum stylet in maintaining the elongate member 11 in the straight configuration.

While a platinum stylet is depicted, a bioresorbable stylet-like member formed from a bioresorbable material, such as polyacrylic acid (PAA), that is also impregnated with a bio-active substance and which is adapted to dissolve or soften on exposure to cochlear fluids, could be utilized with appropriate modification to the elongate carrier member 11. A stiffening polymer stylet could also be utilized which could be impregnated with a bio-active substance. Such a stylet would soften quickly, but not dissolve quickly, with its very slow dissolution rate allowing the drug to effectively elute to the body. Equally, whilst a substantially cylindrical lumen is depicted, the lumen 14 could indeed be any shape necessary to perform the function. Again, the PAA stylet-like member in this invention can have a stiffness that is either sufficient or insufficient to retain the silicone elongate member 11 in a straight configuration as depicted in FIG. 2. It will be appreciated that a bioresorbable stylet-like member could be formed from other suitable bioresorbable materials. A stylet-like member made from a shape memory or heat sensitive material could also be utilised instead of stylet 15.

In the depicted embodiment, the elongate member 11 is adapted to also act as a system for delivery of one or more pharmaceutical or bioactive substances to the cochlea 30. In the depicted embodiment, this system is provided by an additional lumen 21 that acts as a reservoir for a fluid 23 constituting or including the one or more pharmaceutical or bioactive substances. The lumen 21 is pre-filled with the pharmaceutical or bioactive substances during manufacture and then sealed by the plug closure 22.

Provided at the first end 13 of the member 11 is a fluid egress means comprising a valve 24 in the form of a slit formed in the structure of the elongate member 11. Other embodiments with more than one slit 24 can be envisaged. The slit 24 is adapted to allow fluid 23 within the lumen 21 to exit the lumen 21 but prevents fluid flow from external the member 11 back into the lumen 21. To prevent flow of fluid through the slit 24 prior to implantation, the slit is covered with a layer 25 of bioresorbable PAA. Other suitable bioresorbable materials could be envisaged and the material could also be impregnated with the pharmaceutical substance. While only depicted as covering the slit 24, the layer 25 could coat a greater portion or the entire surface of the elongate member 11.

On insertion of the elongate member 11 into the scala tympani 31, the cochlear fluid commences to soften and dissolve the layer 25 of PAA. In addition to lubricating the first end 13, the dissolution of the layer 25 allows the fluid 23 to commence to flow from the lumen 21 into the scala tympani 31.

Figure 6A:
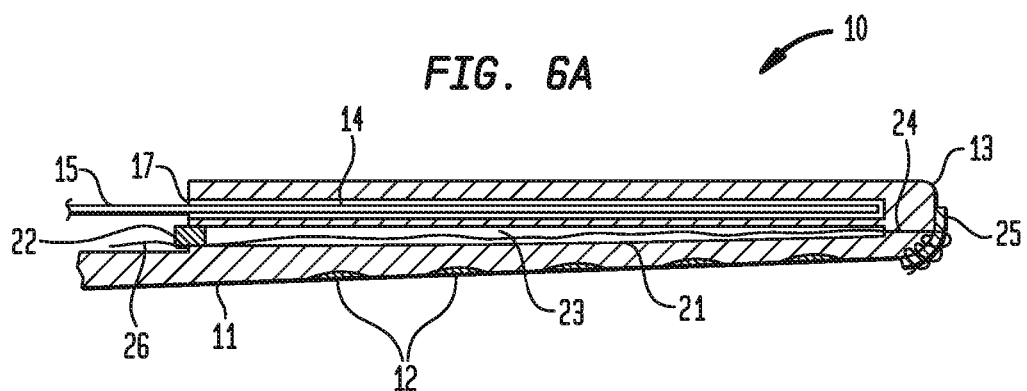
FIGS. 6A and 6B are simplified cross-sectional views of an electrode assembly in accordance with other embodiments of the present invention.
Figure 6B:
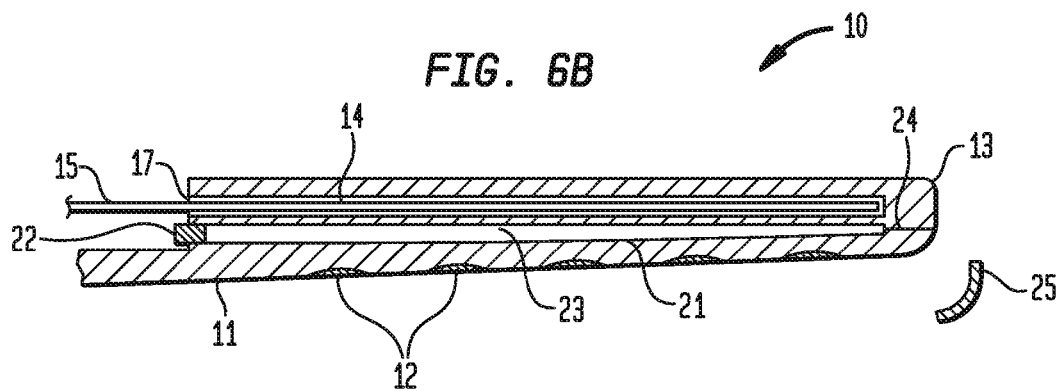

It is also possible that the pharmaceutical or bioactive substance 23 could be released from the lumen 21 by way of a mechanical means. Such a means may include pushing the stylet 15 through the slit 24 at the end of the assembly 10 to break the seal just prior to insertion. As shown in FIGS. 6A and 6B, another method of releasing the pharmaceutical substance would be to include a suture 26 down the lumen 21 and through the seal 25. The suture 26 could then be pulled in an action similar to a "rip-cord" to open the end of the assembly 10.

Figure 4:
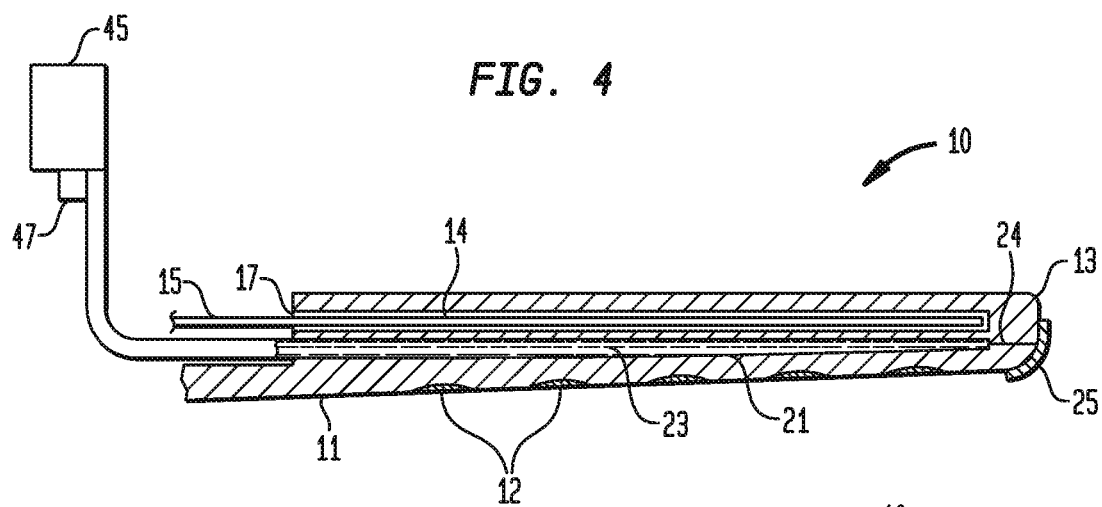
FIG. 4 is a simplified cross-sectional view of an electrode assembly in accordance with another embodiment of the present invention.
Figure 5:
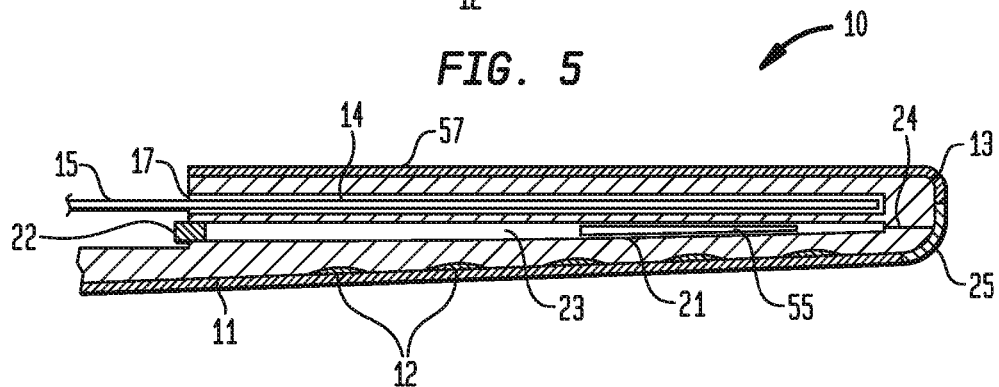
FIG. 5 is a simplified cross-sectional view of an electrode assembly in accordance with a still further embodiment of the present invention.

In the embodiments shown in FIG. 4, lumen 21 is in fluid communication with an additional reservoir 45 for fluid 23. Additional reservoir 45 can be placed under the skin of the implantee and be Tillable by a needle and syringe assembly when required. A pump 47, such as an osmotic pump, can be used to transfer fluid from additional reservoir 45 to lumen 21.

While depicted with a lumen 21, it can also be envisaged that the elongate member 11 could be impregnated with a pharmaceutical agent or other bioactive substance prior to implantation. The pharmaceutical agent or bioactive substance would then be free to leach from the elongate member 11 following insertion. In this embodiment, it can be envisaged that a layer of bioresorbable PAA material may coat the entire impregnated portion of the elongate member 11 so ensuring that the pharmaceutical agent or bioactive substance does not leach from the elongate member 11 prior to implantation.

While the elongate member 11 is manufactured with a preformed curved configuration, the depicted assembly 10 is typically delivered to a surgeon in a sterile package with the stylet 15 and pharmaceutical fluid 23 in place (as depicted in FIG. 2).

On removal from the package and insertion into the scala tympani 31 of the cochlea 30, the cochlear fluids commence to dissolve and soften the layer 25.

As the elongate member 11 is inserted into the scala tympani 31 of the cochlea 30, the surgeon can commence to withdraw the stylet 15 from the lumen 14 through opening 17. On withdrawal of the stylet 15, the elongate member 11 is free to adopt the spiral configuration depicted in FIG. 3 with the electrodes 12 facing the modiola within the cochlea 30 so that they are positioned as close as possible to the spiral ganglia thereof.

The provision of a system for delivering a pharmaceutical substance that promotes healing and/or more efficient neural stimulation while preventing the formation of substantial scar tissue in the cochlea, enhances the likelihood of successful long-term placement of the assembly 10 in the cochlea and subsequent successful use of the cochlear implant by the implantee.

While the preferred embodiment of the invention has been described in conjunction with a cochlear implant, it is to be understood that the present invention has wider application to other implantable electrodes, such as electrodes used with pacemakers.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All documents, patents, journal articles and other materials cited in the present application are hereby incorporated by reference.

It is to be understood that the detailed description and specific examples, while indicating embodiments of the present invention, are given by way of illustration and not limitation. Many changes and modifications within the scope of the present invention may be made without departing from the spirit thereof, and the invention includes all such modifications.

What is claimed is:

1. A cochlear implant, comprising:
   an implantable electrode array assembly implantable proximate to nerve cells of a recipient, comprising:
      a resiliently flexible elongate member,
      a plurality of electrodes disposed on an outer surface of the elongate member,
      a lumen extending through at least a portion of the elongate member, and
      at least one substance egress extending from the lumen to the outer surface of the elongate member;
   a stimulator unit electrically connected to the plurality of electrodes in the implantable electrode array assembly and configured to generate electrical stimulation signals for delivery to a first population of the nerve cells via one or more of the plurality of electrodes;
   a bioactive substance source fluidically coupled to the lumen and configured to provide a bioactive substance to the at least one substance egress for application to a second population of the nerve cells;
   a reservoir configured to store the bioactive substance, wherein the lumen in the implantable electrode array assembly is configured to receive an amount of the bioactive substance from the reservoir;
   a substance delivery mechanism configured to control one or more of the bioactive substance source and the at least one substance egress to cause selective application of the bioactive substance to the second population of nerve cells; and
   a valve configured to control flow of the bioactive substance from the at least one substance egress.

2. The cochlear implant of claim 1, wherein the wherein the first and second populations of nerve cells are the same populations of nerve cells.

3. The cochlear implant of claim 1, wherein at least a portion of the elongate member is impregnated with a bioactive sub stance.

4. The cochlear implant of claim 1, wherein the valve is configured to prevent fluid flow from external the elongate member back into the lumen.

5. The cochlear implant of claim 1, wherein the bioactive substance is selected from the group consisting of a pharmaceutical agent, an anti-inflammatory substance, an antibiotic, and a steroid.

6. The cochlear implant of claim 1, further comprising:
   a sound input component configured to receive a sound signal;
   a sound processor electrically connected to the sound input configured to generate data signals based on the received sound signal,
   a receiver coil electrically connected to the stimulator unit; and
   a transmitter coil electrically connected to the sound processor and configured to transmit the data signals to the receiver coil via a radio frequency link.

7. The cochlear implant of claim 1, wherein the reservoir is configured to be implanted in the recipient external to the elongate member and is fluidically coupled to the lumen.

8. The cochlear implant of claim 1, wherein the reservoir is positioned in the elongate member and is fluidically coupled to the at least one substance egress via the lumen.

9. The cochlear implant of claim 1, wherein the reservoir has a cylindrical shape.

10. The cochlear implant of claim 1, wherein the substance delivery mechanism comprises a pump.

11. The cochlear implant of claim 1, wherein the substance delivery mechanism comprises the valve.

12. The cochlear implant of claim 1, wherein the substance delivery mechanism is configured to control the flow rate of the bioactive substance through the at least substance egress.

13. A method performed by a cochlear implant comprising an implantable electrode array assembly disposed in a cochlea of a recipient, the method comprising:
   generating electrical stimulation signals with a stimulator unit electrically connected to a plurality of electrodes disposed on an outer surface of the implantable electrode array assembly;
   delivering the electrical stimulation signals to a first population of cochlea nerve cells via one or more of the plurality of electrodes;
   delivering a bioactive substance to a second population of cochlea nerve cells via a lumen extending through at least a portion of the implantable electrode array assembly and at least one substance egress extending from the lumen to the outer surface of the implantable electrode array assembly; and
   controlling, via a valve, the release of the bioactive substance from the at least one substance egress.

14. The method of claim 13, wherein the cochlear implant comprises a reservoir fluidically coupled to the at least one substance egress via the lumen, and wherein delivering the bioactive substance to the second population of cochlea nerve cells comprises:
   controlling the release of the bioactive substance from the reservoir.

15. The method of claim 14, wherein the reservoir is implanted in the recipient external to the implantable electrode array assembly and wherein the reservoir is fluidically coupled to the lumen.

16. The method of claim 14, wherein the reservoir is positioned in the implantable electrode array assembly and is fluidically coupled to the at least one substance egress via the lumen.

17. The method of claim 14, wherein controlling the release of the bioactive substance from the reservoir comprises:
   pumping the bioactive substance from the reservoir.

18. The method of claim 13, wherein the first and second populations of nerve cells are the same populations of nerve cells.

* * * * *